(12) United States Patent
Soumyanath Raman et al.

(10) Patent No.: US 7,361,685 B2
(45) Date of Patent: Apr. 22, 2008

(54) COMPOUNDS FOR USE IN THE TREATMENT OF SKIN CONDITIONS

(75) Inventors: Amala Soumyanath Raman, Portland, OR (US); Robert Charles Hider, Clacton-on-Sea (GB); Radhakrishnan Venkatasamy, London (GB)

(73) Assignee: Oregon Health & Science University, Portland, OR (US)

( * ) Notice: Subject to any disclaimer, the term of this patent is extended or adjusted under 35 U.S.C. 154(b) by 63 days.

(21) Appl. No.: 10/466,495

(22) PCT Filed: Jan. 15, 2002

(86) PCT No.: PCT/GB02/00158

§ 371 (c)(1),
(2), (4) Date: Jan. 30, 2004

(87) PCT Pub. No.: WO02/057260

PCT Pub. Date: Jul. 25, 2002

(65) Prior Publication Data

US 2004/0254165 A1    Dec. 16, 2004

(30) Foreign Application Priority Data

Jan. 16, 2001    (GB) ................................. 0101146.9

(51) Int. Cl.
*A61K 31/36* (2006.01)
*C07D 413/10* (2006.01)
(52) U.S. Cl. ..................................... 514/466; 549/440
(58) Field of Classification Search ................ 514/466; 549/440
See application file for complete search history.

(56) References Cited

U.S. PATENT DOCUMENTS 2,326,350 A * 8/1943 Gertler et al. ................ 514/67

FOREIGN PATENT DOCUMENTS

| DE | 27 57 483 B1 | 6/1979 |
| EP | 0 650 728 A1 | 5/1995 |
| JP | 05-262646 | * 10/1993 |
| JP | 6-336417 A1 | 12/1994 |
| JP | 10130203 | 5/1998 |
| WO | WO96/25939 | 8/1996 |
| WO | WO 00/02544 | 1/2000 |

OTHER PUBLICATIONS

Gaind et al. "presevatives IX" Ca 83:72580 (1975).*
Gerter et al. "Insecticides . . . " Ca 38:4019 (1944).*
Nicki et al. "N-isopropyl . . . " CA 71:70345 (1969).*
Watanabe et al. "Peper alkaloids . . . " CA 120:124900 (1994).*
CHEMCAST 2001:281254 (2001) see RN 349578-25-2.*
CHEMCASTS 2005:1985671 (2005) RN 461687-89-8.*

Bennett DC, Cooper P, Hart I (1987) A line of non-tumourigenic mouse melanocytes, syngeneic with the B16 melanoma and requiring a tumour promoter for growth, International Journal of Cancer 39, 414-418.
Donato S, Kesavan M, Austin S, Mohan K and Rajagopalan K (1990) Clinical trial of certain Ayurvedic medicines indicated in vitiligo, Ancient Sci. Life 9, 202-206.
Leung AY (1985) Chinese Herbal Remedies, Publ. Wildwood House, London, UK, pp. 120-123.
Duke JA and Ayensu ES (1985) Medicinal Plants of China, vol. 2 Publ. Reference Publications Inc. Algonac, MI, USA, pp. 483-485.
Johri RK and Zutshi U (1992) An Ayurvedic formulation 'Trikatu' and its constituents, J Ethnopharmacology 37, 85-91.
Dymock W, Warden CJ and Hooper D (1890) Pharmacographia Indica. Ed. Dymock W. Publ. K Paul, Trench and Trübner, London, UK. pp. 166-181.
Kapoor LD (1990) Handbook of Ayurvedic Medicinal Plants, Publ. CRC Press, Boca Raton, FL, USA, pp. 264-266.
The Wealth of India (1969), vol. VIII: Ph-Re. Publ. Publications and information directorate, CSIR, New Delhi, India, pp. 99-118.
Moss VNS (1953) Ayurvedic Flora Indica. Publ. not known. pp. 102-105.
Dutt UC (1989) The Materia Medica of the Hindus, with a glossary of Indian Plants by KBL Sen and KA Sen, 2$^{nd}$ Edition, Publ. Mittal, Dehlhi, India, pp. 241-244.
Dash VB (1983) A Handbook of Ayurveda, Publ. Concept Publishing, pp. 93-97.
Oriowo MA (1982) Anti-inflammatory activity of piperonyl-4-acrylic isobutyl amide, Planta Medica 44, 54-56.
Kirtikar KR and Basu BD (1935) Indian Medicinal Plants, 2$^{nd}$ edition. Eds. E Blatter, JF Caius and KS Mhaskar, Publ. Lalit Mohan Basu, Allahabad, India, pp. 2128-2130 and 2133-2135.
Raman A and Lin Z (1996) ACTIVE Ingredients Conference Proceedings, Le Palais des Congrès de Paris, France Nov. 13-14, 1996, Publ. Verlag fuer Chemische Industrie H. Ziolkowsky GmbH Augsburg, Germany pp. 203-221.

(Continued)

*Primary Examiner*—Celia Chang
(74) *Attorney, Agent, or Firm*—Schwabe, Williamson & Wyatt, P.C.

(57) ABSTRACT

The present invention provides compounds of formula (I) and analogues or derivatives thereof for the treatment of skin conditions, such as Vitiligo, which are treatable by the stimulation of melanocyte proliferation and also for treating skin cancer. The compounds may also be used to cosmetically enhance the natural coloration of the skin

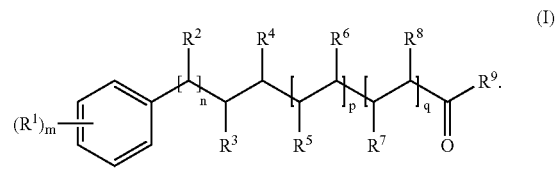

14 Claims, No Drawings

OTHER PUBLICATIONS

Nadkarni AK (1976) Dr KM Nadkarni's Indian Materia Medica, vol. 1, Publ. Popular Prakashan, Bombay, India, pp. 960-972 and 1267-1270.

Parmar VS, Jain SC, Bisht KS et al., (1997), Phytochemistry of the genus *Piper* (Review), Phytochemistry 46, 597-673.

Weatherall DJ, Ledingham JGG, Warrell DA Eds. (1996), Oxford Textbook of Medicine, 3rd edition, Publ. Oxford University Press, Oxford, Section 23, pp. 3755-3759.

Raman A, Lin Z, Hoult JRS, Identification of a phytochemical stimulant for the proliferation of mouse melanocytes in culture, J. Pharm. Pharmacol. 50 (Supplement), 247.

Lin Z, Donatien P, Raman A, Bennett DC (1998) A naturally occuring growth promoter for human melanoblasts in culture, J. Pharm. Pharmacol. 50 (Supplement), 218.

Lin Z, Hoult JRS, Bennett DC, Raman A (1999) Stimulation of mouse melanocyte proliferation by *Piper nigrum L*. fruit extract and its main alkaloid, piperine, Planta Medica 65, 600-603.

WPI Abstract Accession N° 97 061723/06; Chemical Abstracts Accession N° *126*: 94788, Derwent Abstract JP08310949 (YAKULT) Nov. 26, 1996 & JAPIO Abstract.

WPI Abstract Accession N° 96-318931/32; Derwent Abstract JP08143562 (CADILA) Jun. 4, 1996 & JAPIO Abstract.

Raman A, Lin Z and Hoult JRS (1998), Identification of a phytochemical stimulant for the proliferation of mouse melanocytes in culture, Poster displayed at 135th British Pharmaceutical Conference, Eastbourne, UK, Sep. 8-11, 1998.

Lin Z, Donatien P, Raman A and Bennett DC (1998) Piperine, a naturally occurring growth promoter for human melanoblasts in culture, Poster displayed at 135th British Pharmaceutical Conference, Eastbourne, UK, Sep. 8-11, 1998; and at 39th Annual meeting of the American Society of Pharmacognosy, Orlando, Jul. 19-24, 1998.

A Raman, Z Lin and JRS Hoult, A mouse melanocyte proliferation stimulation from Piper nigrum L., "2000 Years of Natural Product Research—Past, Present, Future", Post displayed at Joint meeting of the American Society of Pharmacognosy, Association Francaise pour L'Enseignement et La Recherche en Pharmacognoise, Gesellschaft fuer Arzneipflanzenforschung and the Phytochemical Society of Europe, Amsterdam, The Netherlands, Jul. 26-30, 1999.

Lin ZX, Hoult JRS, Raman A (1999) Sulphorhodamine B assay for measuring proliferation of a pigmented melanocyte cell line . . . , J. Ethnopharmacology 66, 141-150.

Database CA Online, Chemical Abstracts Service, Columbus, Ohio, US; Gaind, K.N. et al., "Preservatives IX"; retrieved from STN, Database accession No. 83:72580.

De Paula, Vanderlucia F. et al., Synthesis and insecticidal activity of new amide derivatives of piperine, Pest Management Science (2000), 56(2), 168-174.

\* cited by examiner

COMPOUNDS FOR USE IN THE TREATMENT OF SKIN CONDITIONS

CROSS-REFERENCE TO RELATED APPLICATIONS

This application is the U.S. national phase of PCT/GB02/00158, filed Jan. 15, 2002, which claims priority to GB Serial No. 0101146.9, filed Jan. 16, 2001, each of which is incorporated herein by reference in its entirety.

FIELD OF THE INVENTION

This invention relates to the treatment of skin conditions, comprising those conditions requiring stimulation of melanocyte proliferation and to the inhibition of melanomas. The invention is of especial application to the treatment of vitiligo and skin cancer.

Vitiligo is a common skin pigment disorder characterised by the development of patchy de-pigmented lesions. Current treatments which include the use of photosensitisers (eg psoralens) with UVA radiation (PUVA), corticosteroids or skin grafting have low success rates and are generally accompanied by unpleasant side effects. Vitiligo has a highly detrimental impact on the emotional well-being of the sufferer, the disfiguring effects of the disease being compounded by the absence of a suitable treatment. Although vitiligo patches are not believed to contain melanocytes (pigment producing cells), a reservoir exists in hair follicles in vitiliginous skin. Thus activation of hair follicular melanocytes is a crucial process in the repigmentation of vitiliginous skin.

Certain plant remedies, usually administered as mixtures of herbs or extracts, particularly those used in traditional Chinese medicine and Indian Ayurvedic medicine, have been employed for the treatment of vitiligo for a long time and in many cases have given positive results in small scale studies. Herbs such as *Psoralea corylfolia* L. and *Vernonia anthelmintica* Willd. (=*Centratherum anthelminticum* Kuntze) are well known for their use in this disease. Psoralens, which are employed in the modern PUVA and khellin in KUVA therapy were originally derived from plant sources (*Psoralea corylifolia* L and *Ammi visnaga* respectively) used in traditional remedies for vitiligo. However these therapies rely on the use of UV irradiation for their efficacy, which is associated with the aetiology of skin cancer.

The fruit of black pepper (*Piper nigrum* L.) and long pepper (*Piper longum* L.) are both important medicinal herbs in Ayurvedic and Unani (traditional Indian) medicine systems, in which remedies generally consist of mixtures of herbs. A wide range of the medicinal uses of black pepper have been documented by Kirtikar and Basu (Indian Medicinal Plants, 2$^{nd}$ Edition, Vol. 3, (1935) pages 2128-2135), including its use in the treatment of leucoderma. Black pepper has also been implicated as a possible adjunct to *Vernonia anthelmintica* in the treatment of leucoderma (Indian Medicinal Journal, Vol. 1, 3$^{rd}$ Edition, (1982) 1267-1270). These two herbs are employed as a constituent in many traditional herbal preparations for a variety of uses, including gastro-internal and skin ailments. Compositions comprising black pepper, ginger and pipali have been used in the treatment of vitiligo (Ancient Science of Life, Vol. IX, No. 4 (1990) 202-206); however, the specific therapeutic action of black pepper in this orally administered composition has not been established.

It has been found (WO 001/02544) that, piperine, which is present in the frit of *Piper nigrum*, stimulates the replication of melanocytes. The action of piperine is to increase the number of cells which confer pigmentation. Piperine is the compound (EE)-1-[5-1,3-benzodioxol-5-yl)-1-oxo-2,4-pentadienyl]piperidine and should not be confused with piperidine.

Pharmaceutical compositions containing piperine have been used in the treatment of tuberculosis and leprosy (EP 0 650 728). It has also been suggested that piperine is able to enhance the bioavailability of the other constituents of a pharmaceutical composition (WO 96/25939).

There is, therefore, a need for further compounds and compositions, which are able to stimulate the proliferation of melanocytes.

SUMMARY OF THE INVENTION

The invention provides a compound or formula (1) for use in the treatment of a skin condition requiring stimulation of melanocyte proliferation and melanomas, in which

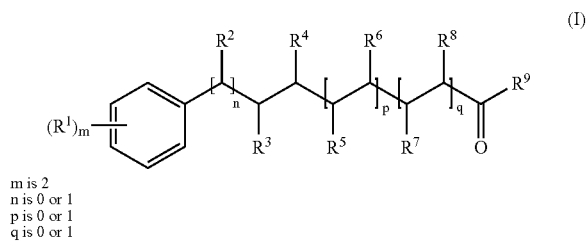

m is 2
n is 0 or 1
p is 0 or 1
q is 0 or 1 the two $R^1$ groups together represent a 3',4'-methylenedioxy group
$R^2$ is hydrogen
$R^3$ and $R^4$ represent hydrogen atoms or together represent a carbon to carbon double bond;
$R^5$ and $R^6$ represent hydrogen atoms or together represent a carbon to carbon double bond;
$R^7$ and $R^8$ represent hydrogen atoms or together represent a carbon to carbon double bond; and
$R^9$ represents piperidino, morpholino, cyclohexylamino, methylamino, ethylamino and isopropylamino in any of its E, Z geometrically isomeric forms or an active analogue or derivative thereof as hereinafter defined or optionally when n is 1 $R^2$ and $R^3$ together represent a carbon to carbon double bond and one or more of $R^4$ and $R^5$ together, $R^5$ and $R^6$ together, $R^6$ and $R^7$ together or $R^7$ and $R^8$ together represent a carbon to carbon double bond the other of $R^4$ to $R^8$ representing hydrogen with the proviso that the compound is not piperine, 3,4-dihydropiperine; 1,2,3,4-tetrahydropyridine, Ilepeimide or piperettine.

The invention also provides the use of a compound of formula (I) in the preparation of a medicament for use in the treatment of a skin condition requiring stimulation of melanocyte proliferation and melanomas. Pharmaceutical compositions comprising a compound of formula (I) and a pharmaceutically acceptable carrier are also provided.

The active ingredient may be used on its own, but is more suitably used in combination with a carrier or excipient and optionally one or more further active ingredients.

Stimulation of melanocyte proliferation greatly facilitates the re-pigmentation of de-pigmented skin, e.g. post traumatised de-pigmented skin. The term "post traumatised de-pigmented skin" means the skin formed during the healing process that occurs after a skin trauma. De-pigmentation may arise, for example, from scar tissue formed as a result of a skin trauma such as burn or other skin lesion or may be due to vitiligo. The present invention can be used to treat any of these skin disorders in a patient.

Generally in this invention, the compounds of formula (I) or active derivatives or analogues thereof may be administered by oral, topical, intravenous or subcutaneous (intramuscular) routes but are preferably applied topically (to the area of the skin where treatment is desired). Indeed, the twice-daily topical application of compounds of formula (I) has been found to induce significant pigmentation in mice. Skin coloration in the mouse population under study was first observed at approximately four weeks after the treatment was started. This coloration was enhanced further as a result of subsequent topical applications.

The active ingredient may be formulated as a solid powder, a paste, ointment or cream; a tablet or capsule or a solution.

The compounds of formula (I) may also be used to treat a person having a skin condition which would benefit from coloration, e.g. to enhance or promote the natural colouring of the skin. The treatment may be used for prophylactic, therapeutic or cosmetic purposes.

The compounds of formula (I) and their analogues or derivatives as hereinafter defined inhibit the proliferation of melanoma cells. Thus, they may also be used in the treatment of skin cancer. Another aspect of the invention therefore provides a method of treating skin cancer in a human or animal patient comprising the administration to said patient of a therapeutically effective amount of a compound of formula (I) or an active analogue or derivative thereof as hereinafter defined.

The compounds of formula (I) or active analogues or derivatives thereof may be administered by oral or topical routes. Suitable dosage forms may be any of those discussed above.

Certain of the active analogues or derivatives of the compound of formula (1) are new. The present invention therefore includes such compounds, and pharmaceutical compositions containing them together with a carrier or excipient

DESCRIPTION OF THE PREFERRED EMBODIMENTS

Preferred compounds of formula (I) are those in which
(a) n is 0, one of p or q is other than 0, $R^3$ and $R^4$ together form the second bond of a carbon to carbon double bond and either $R^5$ and $R^6$ together or $R^7$ and $R^8$ together form the second bond of a carbon to carbon double bond; and
(b) n is 0, one of p or q is other than 0, $R^3$ and $R^4$ are each hydrogen and either $R^5$ and $R^6$ or $R^7$ and $R^8$ are also hydrogen and $R^9$ is cyclohexylamino or piperidino.
Particularly preferred compounds are those in which
(a) n is 0, one of p or q is other than 0, $R^3$ and $R^4$ together form the second bond of a carbon to carbon double bond and either $R^5$ and $R^6$ together or $R^7$ and $R^8$ together form the second bond of a carbon to carbon double bond and $R^9$ is selected from morpholino, cyclohexylamino, methylamino, ethylamino and isopropylamino;
(b) n is 0, p is 0, q is 1, $R^3$, $R^4$, $R^7$ and $R^8$ represent hydrogen and $R^9$ is cyclohexylamino; and
(c) n is 0, p is 1, q is 1, $R^3$, $R^4$, $R^5$, $R^6$, $R^7$ and $R^8$ represent hydrogen and $R^9$ is piperidino.

The compounds of formula (1) can be prepared from the appropriate acid with the appropriate connecting chain between the carboxylic acid function and the benzene ring and having the appropriate stereochemistry. Where necessary, this may be preceded or followed by reduction to reduce the double bond or bonds in the connecting chain. Methods of preparing amides and esters from these acids are illustrated by the Examples below. They may also be adapted from the references cited herein, the disclosure of which is herein incorporated by reference.

The active compounds may be formulated for topical use in the form of creams, soft paraffin or lotions. Aqueous cream BP or Yellow Soft Paraffin BP may suitably contain the active at 0.03-3.0 mg % w/w or an equivalent amount of plant extract. A suitable lotion is typically prepared from 20% glycerol and 80% ethanol in purified water and contains 0.03-3.0 mg % w/w of the active material. These topical formulations may also contain penetration enhancers such as oleic acid, propylene glycol, ethanol, urea, lauric diethanolamide or azone, dimethyl sulphoxide, decylmethyl sulphoxide, or pyrrolidone derivatives. Liposomal delivery systems may also be used.

Compositions for oral formulation include tablets or capsules containing 1.5-150 mg active for daily administration.

The invention will now be described with reference to the following non-limiting examples, with reference to the accompanying tables and drawings.

EXAMPLES

Introduction

Cell Culture Experiments

Microplate Culture and Sulforhodamine B (SRB) Assay

Cells of mouse melan-a cell line (passage number 18-24), a first known line of non-tumorigenic pigmented mouse melanocytes were maintained in a flask (Costar, Cambridge, Mass., USA) using RPMI 1640 (ICN, Costa, Mesa, Calif., USA) as a basic medium. For microplate proliferation assays, subconfluent melan-a cultures were trypsinized (0.25% trypsin at 37° C. for 5-10 min) and inoculated with a repeater-pipettor (Finn pipette, Labsystems, Finland) into 96-well microtiter plates (Costar, Cambridge, Mass., USA) at a seeding concentration of 6×10 cells per well. A supplemental growth medium of 10% foetal bovine serum (FBS) was added to the 36-well microtiter plates. The plates were incubated at 37° C. in a 10% $CO_2$, 90% air humidified atmosphere for 4 days. At the end of the incubation, an SRB assay was performed. Briefly, cells attached to the bottom of the plate were fixed by addition of cold trichloroacetic acid (TCA, 4° C., Aldrich, Dorset, UK) on the top of the growth medium (final TCA 20% w/v). The plate was placed at 4° C. for 1 hour before being gently washed five times with tap water. It was allowed to dry in air, or aided with a hair dryer to speed up the drying process, then 50 µl of 4% w/v SRB dissolved in 1% acetic acid in water was added to each well for 30 min. At the end of the staining period, unbound SRB was removed by washing 4 times with 1% acetic acid. The plate was air dried again, and 150 µl of 10 mM aqueous Tris base (Sigma-Aldrich Co. Ltd, Irvine, UK) was added into each well to solubilize the cell-bound dye. The plate was shaken for 15 min on a gyratory shaker followed by reading the optical density (OD) at 550 nm in a microplate spectrophotometer (Anthos Labtec HT3, version 1.06). A control assay was carried out on cells incubated without test compound. There were 2 or 3 series of experiments, each of which consisted of six replicate experiments. The results are tabulated below.

Example 1

Compounds of Formula (1)

1.0 Introduction

Vitiligo is defined as a circumscribed, acquired, idiopathic, progressive hypomelanotic skin disorder which is characterised by the development of patchy depigmented macules due to progressive loss of melanocytes which is often familial with lack of established aetiology.

Various compounds of formula (1) were synthesised and tested for melanocyte (mouse melan-a) proliferant activity in-vitro. Cells were incubated with the test compound for 4 days, as described above.

1.1 Percentage Cell Growth (A)

Percentage cell growth was obtained with a given compound calculated as (optical density in the presence of the compound/control optical density)×100.

1.2 Relative Activity to Piperine

Melan-a cell proliferant activity for tested compounds was compared with that obtained with piperine. Percentage stimulant activity is (A-100) where A stands for piperine or a test compound's percentage cell growth (see 1.1). All figures are given with Standard Error of the Mean.

Relative activity to piperine was calculated as (A-100) compound/(A-100) piperine).

Interpretation of the relative active value is as follows
<0—Inhibition of cell growth
0—No effect (equal to control)
0-1—Stimulant but weaker effect than piperine
1—Equal stimulant effect to piperine
>1—Stimulant and stronger effect than piperine 1.3 Dendricity Effect on dendricity of melan-a cells by the test compounds was by observation under microscope. Dendricity is relevant to vitiligo since normal skin melanocytes have dendrites, but in vitiligo the melanocytes seem to lose these before they disappear from the patches.

1.4 Synthesis of Compounds of Formula (1)

The compounds of formula (1) were synthesised using methods described in the literature, adapted from the literature or devised in the inventors' laboratory. Structures of compounds were verified using NMR, MS, IR spectroscopy and melting point Unless a synthetic method is given, reagents and reactants were purchased from Sigma Aldrich.

1.5 Results

The activity of compounds of formula (I) at a single concentration of test compound (10 μM) is shown in Table 1. This is followed by data showing results at other concentrations. Many compounds showed a "cross-over" effect in which the test compound was less active than piperine at 10 μM but more active at 50 μM.

TABLE 1

| | | Effect on melan-a cells at μM concentration | | | | |
| --- | --- | --- | --- | --- | --- | --- |
| Varation of Nitrogen Substituent of Piperine | | Percentage cell growth (Repeated experiments) | | Stimulant activity | Relative activity to piperine | Dendricity |
| Code No | Structure | Test cpd. | Piperine | | | |
| RV-A02 | [structure] | 156 ± 58<br>187 ± 40<br>153 ± 19 | 210 ± 65<br>170 ± 22<br>155 ± 19 | Positive | 0.5<br>1.02<br>0.9 | +++ |
| RV-A07 | [structure] | 170 ± 24* | 216 ± 33* | Positive | 0.6 | ++ |
| RV-A08 | [structure] | 200 ± 14 | 236 ± 17 | Positive | 0.73 | +++ |

TABLE 1-continued

| | | Effect on melan-a cells at μM concentration | | | | |
|---|---|---|---|---|---|---|
| Varation of Nitrogen Substituent of Piperine | | Percentage cell growth (Repeated experiments) | | Stimulant activity | Relative activity to piperine | Dendricity |
| Code No | Structure | Test cpd. | Piperine | | | |
| RV-A09 | [structure: methylenedioxyphenyl-diene-C(O)NH-isopropyl] | 224 ± 19 | 263 + 16** | Positive | 0.76 | +++ |
| RV-A10 | [structure: methylenedioxyphenyl-diene-C(O)NH-cyclohexyl] | 308 ± 29** | 302 ± 17** | Positive | 1.02 | +++ |

*P < 0.05, **P < 0.01 compared to vehicle treatment (Dunnett's test) +++ highly dendritic, ++ moderately dendritic, + weakly dendritic, − no effect

| Code No | Structure |
|---|---|
| RV-A02 | [structure: methylenedioxyphenyl-diene-C(O)-morpholine] |

| Compounds Tested | 1 μM | 10 μM | 25 μM | 50 μM |
|---|---|---|---|---|
| Piperine | 147 ± 11**♦ | 192 ± 13**♦ | 167 ± 19** | 142 ± 15** |
| RV-A02 | 125 ± 10 | 167 ± 17** | 171 ± 8** | 168 ± 12**□ |

**P < 0.01 Compared to vehicle treatment (Dunnet's t test)
♦Piperine is significantly more active than test compound P < 0.05
□Test compound is significantly more active than Piperine P < 0.05

| Code No | Structure |
|---|---|
| RV-A08 | [structure: methylenedioxyphenyl-diene-C(O)NH-ethyl] |

| Compounds Tested | 1 μM | 10 μM | 50 μM | 100 μM |
|---|---|---|---|---|
| Piperine | 216 ± 14**♦ | 236 ± 17** | 61 ± 11 | 32 ± 5 |
| RV-A08 | 139 ± 27** | 200 ± 14** | 81 ± 12 | 62 ± 13 |
| Dendricity of RV-A08 | ++ | +++ | + | + |

**P < 0.01 Compared to vehicle treatment (Dunnet's t test)
♦Piperine is significantly more active than test compound P < 0.05
+++ highly dendiitic, ++ moderately dendritic, + weakly dendritic

| Code No | Structure |
|---|---|
| RV-A07 | [structure: methylenedioxyphenyl-diene-C(O)NH-methyl] |

| Compounds Tested | 1 μM | 10 μM | 50 μM | 100 μM |
|---|---|---|---|---|
| Piperine | 211 ± 16**♦ | 216 ± 33** | 52 ± 15 | 16 ± 3 |
| RV-A07 | 140 ± 12** | 170 ± 24** | 71 ± 5 | 46 ± 2 |
| Dentricity of RV-A07 | ++ | ++ | + | + |

**P < 0.01 Compared to vehicle treatment (Dunnet's t test)
♦Piperine is significantly more active than test compound P < 0.05
++ moderately dendritic, + weakly dendritic

| Code No | Structure |
|---|---|
| RV-A09 | [structure: methylenedioxyphenyl-diene-C(O)NH-isopropyl] |

| Compounds Tested | 1 μM | 10 μM | 50 μM | 100 μM |
|---|---|---|---|---|
| Piperine | 221 ± 17**♦ | 263 ± 16** | 77 ± 12 | 24 ± 2 |
| RV-A09 | 187 ± 15** | 224 ± 19** | 85 ± 5 | 42 ± 6 |
| Dendricity of RV-A09 | +++ | +++ | + | + |

**P < 0.01 Compared to vehicle treatment (Dunnet's t test)
♦Piperine is significantly more active than test compound P < 0.05
+++ highly dendritic, + weakly dendritic

| RV-A10 | | | | |
|---|---|---|---|---|
| Code No | Structure | | | |
| RV-A10 | ![structure] | | | |
| Compounds Tested | 1 µM | 10 µM | 50 µM | 100 µM |
| Piperine | 236 ± 30** | 302 ± 17** | 78 ± 11 | 21 ± 4 |
| RV-A10 | 301 ± 20**□ | 308 ± 29** | 155 ± 22**□ | 100 ± 13 |
| Dendricity of RV-A10 | +++ | +++ | ++ | + |

**P < 0.01 Compared to vehicle treatment (Dunnet's t test)
□Compound is significantly more active than piperine P < 0.05
+++ highly dendritic, ++ moderately dendritic, + weakly denciritic

| RV-C04 | | | | |
|---|---|---|---|---|
| Code No | Structure | | | |
| RV-C04 | ![structure] | | | |
| Compound | 1 µM | 10 µM | 50 µM | 100 µM |
| Piperine | 191 ± 12**♦ | 216 ± 18** | 184 ± 6** | 96 ± 6 |
| RV-C04 | 129 ± 6** | 192 ± 6** | 192 ± 10** | 191 ± 12** |
| Dendricity of RV-C04 | + | +++ | +++ | +++ |

| RV-C05 | | | | |
|---|---|---|---|---|
| Code No | Structure | | | |
| RV-C05 | ![structure] | | | |
| Compound | 1 µM | 10 µM | 50 µM | 100 µM |
| Piperine | 161 ± 13** | 192 ± 2**♦ | 189 ± 15** | 87 ± 13 |
| RV-C05 | 118 ± 1 | 160 ± 5**♦ | 158 ± 19** | 113 ± 15 |
| Dendricity of RV-C05 | + | ++ | ++ | + |

2. Synthesis of Amide Derivatives of Piperinic Acid 2.1 Preparation of Piperinic Acid (RV-A00)

To piperine (1) (2 g, 0.7 mmol, 1 eq), 20% of methanolic KOH (100 ml) was added and refluxed for 2 days. After completion of the hydrolysis, methanol was removed under reduced pressure and a yellow coloured oily solid was obtained. This residue was dissolved in water (50 ml) and acidified with 6N HCl to pH<1 yielding a yellowish precipitate of piperinic acid. Recrystallization from methanol gave yellow needles (0.9 g, 60% yield). m.p. 206° C.-208° C. (Lit m.p. 217° C.-218° C.)[1]

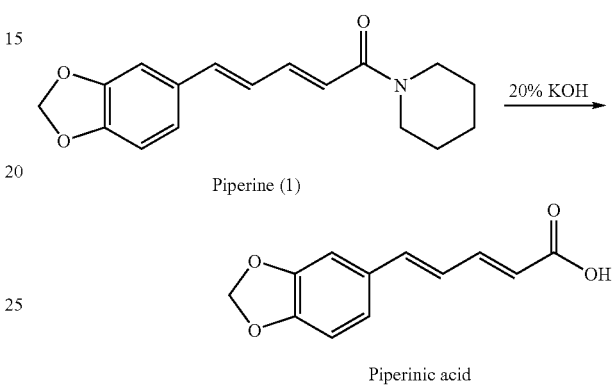

Piperine (1)

Piperinic acid 2.2 Synthesis of Amide Derivatives of Piperinic Acid

The following amines were reacted with piperinic acid in accordance with the following procedure: morpholine; methylamine; ethylamine; isopropylamine and cyclohexylamine. A mixture of piperinic acid (1 eq) and triethylamine (2 eq) in dichloromethane (50 ml) was stirred for 15 min at 0° C. To this mixture methanesulfonyl chloride (1.5 eq) was added and stirred for further 30 min at 0° C. The amine (1.5 eq) was added to the mire and stirred for 1 h at 0° C. and 2 h at room temperature. Dichloromethane (50 ml) was added to the mixture which was then washed with 5% HCl (3×100 ml), saturated aqueous NaHCO₃ (3×100 ml) and water (3×100 ml). The organic fraction was dried over anhydrous sodium sulphate, filtered and rotary evaporated to yield a yellowish solid residue. Recrystallisation from ethylacetate/ petroleum spirit yielded colourless needles of piperlonguminine (120 mg, 32% yield)[2]. The reaction is presumed to proceed through a mesylate ester intermediate.

5-E,E-piperinoyl morpholine (RV-A02)

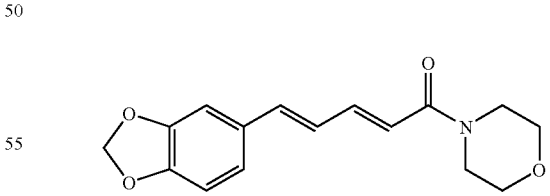

$^1$H-NMR (CDCl$_3$) δ: 6.37 (d, 1H, J=14.6, CH=CH—CH=CH), 7.45 (d, d, 1H, J=10.2, 14.6, CH=CH—CH=CH), 6.72 (d, d, 1H, J=15.5, 10.2, CH=CH—CH=CH), 6.79 (d, 1H, J=15.5 CH=CH—CH=CH), 6.98 (d, 1H J=1.5, Ar-7-H), 6.80 (d, 1H J=8.0, Ar-10-H), 6.89 (d, d, 1H J=1.5, 8.0 Ar-11-H), 5.98 (s, 2H, O—CH$_2$—O), 3.70 (t, 2H, J=4.0 CH$_2$—N—CH$_2$ (morpholine)) 3.60 (t, 2H, J=4.0 CH$_2$—O—CH$_2$ (morpholine)) $^{13}$C-NMR (CDCl$_3$): 42.3 (CH$_2$), 46.1 (CH$_2$), 66 (CH$_2$), 66 (CH$_2$), 101.3 (CH$_2$), 106.5 (CH), 108.5 (CH), 118.7 (CH), 122.7 (CH), 124.9 (CH), 130.8 (C), 139.1 (CH), 143.4 (CH), 148.2 (C), 148.3 (C), 165.6 (C) MS m/z (%): 287 (M+ 57), 201 (100), 173 (25), 171 (10) 143 (10), 115 (30) IR (KBr): $v_{max}$ (carbonyl group) 1641 m.p. 161.8°-162.5° C. (Lit m.p. 167-168° C.)[3], yield 44.1%

5-E,E-piperinoylmethylamine (RV-A07)

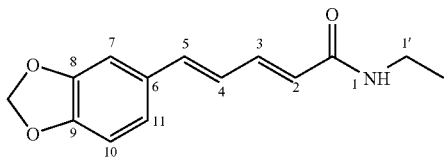

$^1$H-NMR (CDCl$_3$) δ: 5.91 (d, 1H, J=14.8, CH=CH—CH=CH), 7.36 (d, d, 1H, J=10.7, 14.8, CH=CH—CH=CH), 6.66 (d, d, 1H, J=15.4, 10.6, CH=CH—CH=CH), 6.77 (d, 1H, J=15.4 CH=CH—CH=CH), 6.97 (d, 1H, J=1.5, Ar-7H), 6.77 (d, 1H, J=8.0, Ar-10H), 6.88 (d, d, 1H J=1.6, 8.0 Ar-11H), 5.97 (s, 2H, O—CH$_2$—O), 2.91 (t, 3H, CH$_3$), 5.61 (br, NH) $^{13}$C-NMR (CDCl$_3$): 26.9 (CH$_3$), 101.7 (CH$_2$), 106.1 (CH), 108.9 (CH), 123.0 (CH), 123.3 (CH), 125.0 (CH), 131.2 (C), 139.2 (CH), 141.4 (CH), 148.6 (C), 148.6 (C), 167.2 (C) MS m/z (%): 231 (M+89), 201 (42), 173 (67), 172 (32), 171 (17), 143 (27), 116 (21) 115 (100), 89 (12) m.p. 181.1°-182.4° C. (Lit m.p. 186° C.)[5], yield 48.2%

5-E,E-piperinoylmethylamine (RV-A08)

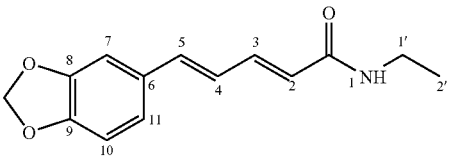

$^1$H-NMR (CD$_3$OD) δ: 6.14 (d, 1H, J=15.0, CH=CH—CH=CH), 7.37 (d, d, 1H, J=10.2, 15.0, CH=CH—CH=CH), 6.93 (d, d, 1H, J=15.7, 10.6, CH=CH—CH=CH), 6.87 (d, 1H, J=15.7 CH=CH—CH), 6.97 (d, 1H, J=1.5, Ar-7H), 6.77 (d, 1H J=8.0, Ar-10H), 6.88 (d, d, 1H J=1.6, 8.0 Ar-11H), 5.97 (s, 2H, O—CH$_2$—O), 3.39 (m, 2H, J=6.2, CH$_2$), 1.22 (t, 3H, J=6.1, CH$_3$), $^{13}$C-NMR (CDCl$_3$): 14.7 (CH$_3$), 36.9 (CH$_2$), 103.2 (CH$_2$), 107.2 (CH), 109.8 (CH), 121.2 (CH), 124.9 (CH), 125.9 (CH), 132.4 (C), 142.9 (CH), 145.2 (CH), 150.2 (C), 150.6 (C), 170 (C)

MS m/z (%): 245 (M+78), 218 (34), 201 (71), 200 (49), 174 (64), 173 (80), 172 (76), 171 (65), 143 (75), 116 (68), 115 (100) m.p. 158.5°-159.9° C. (Lit m.p. 162°-164° C.)[4], yield 45.6%

5-E,E-piperinoylisopropylamine (RV-A09)

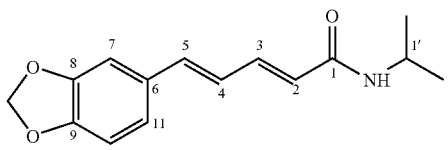

$^1$H-NMR (CDCl$_3$) δ: 5.87 (d, 1H, J=14.8, CH=CH—CH=CH), 7.36 (d, d, 1H, J=10.7, 14.8, CH=CH—CH=CH), 6.66 (d, d, 1H, J=15.4, 10.6, CH=CH—CH=CH), 6.76 (d, 1H, J=15.2 CH=CH—CH=CH), 6.97 (d, 1H J=1.6, Ar-7H), 6.77 (d, 1H J=8.0, Ar-10H), 6.88 (d, d, 1H J=1.6, 8.0 Ar-11H), 5.97 (s, 2H, O—CH$_2$—O), 4.15 (m, 1H, J=6.6, CH), 5.36 (d, 1H, J=7.3 NH), 1.19 (d, 6H, J=6.6, (CH$_3$)$_2$) $^{13}$C-NMR (CDCl$_3$): 23.2 (CH$_3$)$_2$, 41.9 (CH), 101.9 (CH$_2$), 106.4 (CH), 108.9 (CH), 123.0 (CH), 123.8 (CH), 124.1 (CH), 131.3 (C), 140.2 (CH), 141.2 (CH), 148.8 (C), 148.6 (C) 165.6 (C) MS m/z (%): 259 (M+80), 201 (62), 174 (34), 173 (74), 172 (31), 171 (15), 143 (30), 116 (16), 115 (100) m.p. 169°-169.4° C. (Lit m.p. 171°-173° C.)[4], yield 52%

5-E,E-piperinoyl cyclohexylamine (RV-A10)

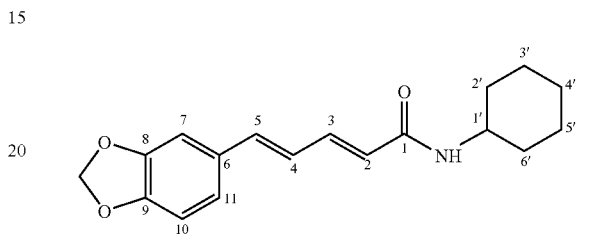

$^1$H-NMR (CDCl$_3$) δ: 5.93 (d, 1H, J=14.8, CH=CH—CH=CH), 7.35 (d, d, 1H, J=10.6, 14.8, CH=CH—CH=CH), 6.66 (dd, 1H, J=15.3, 10.6, CH=CH—CH=CH, 6.76 (d, 1H, J=15.4 CH=CH—CH=CH), 6.96 (d, 1H J=1.6, Ar-7H), 6.76 (d, 1H J=8.0 Ar-10H), 6.87 (d, d, 1H J=1.6, 8.0 Ar-11H), 5.97 (s, 2H, O—CH$_2$—O), 3.87 (m, 1H, CH (cyclohexyl)) 1.99 (m, 2H, CH$_2$(cyclohexyl)) 1.65 (m, 4H, CH$_2$—CH$_2$(cyclohexyl)) 1.39 (m, 2H, CH$_2$ (cyclohexyl)) 1.18 (m, 2H, CH$_2$(cyclohexyl)) 5.48 (d,J=8.0 NH) $^3$C-NMR (CDCl$_3$): 25.3 ((CH$_2$)$_2$), 25.9 (CH$_2$), 33.6 ((CH$_2$)$_2$), 48.6 (CH), 101.3 (CH$_2$), 101.7 (CH), 106.1 (CH), 108.9 (CH), 123.0 (CH), 124.0 (CH), 125.1 (CH), 131.3 (C), 139.0 (CH), 141.2 (CH), 148.5 (C), 148.5 (C), 165.5 (C) MS m/z (%): 299 (M+56), 259 (48) 216 (33), 201 (60), 174 (33), 173 (61), 172 (18), 171 (16), 143 (17), 115 (100) m.p. 196.4°-197.3° C. (Lit m.p. 199°-200° C.)[4], yield 57.4%

REFERENCES

[1] Chatterjee, A., and Dutta, C. P. (1967). Alkaloids of *Piper longum* Linn-I Structure and synthesis of piperlongumine and piperlonguminine, Tetrahedron, 23, 1769-1781.

[2] Nokio Nakumara, Fumiyuki Kiuchi, and Yoshisuke Tsuda (1988). Infrared spectra of conjugated amides: Reassignment of the C=O and C=C absorptions: Chemical and Pharmaceutical Bulletin, 36, 2647-2651.

[3] H. Oediger and A. Schulze (Bayer AG), (1979), Deutsche Auslegeschrift 2757 483

[4] Paula, Vanderlucia F. de; A Barbosa, Luiz C. de; Demuner, Antonio J.; Pilo-Veloso, Dorila; Picanco, Marcelo C. (2000) Pest Management Science 56, 2, 168-174.

[5] Gokale et al., (1948) Journal of University Bombay Science 16/5A 32-35

4. Preparation of 5-(3,4-methylenedioxy phenyl)-pentanoic acid cyclohexylamide (RV-C04)

To 5-(3,4-methylenedioxyphenyl)-2E,4E-pentadienoic acid cyclohexyl amide (300 mg) was added 5% Pd/C (30 mg) and hydrogenated the contents at 30 psi for 1 hr. The solution was filtered and rotary evaporated to yield a white solid. Recrystallisation from ethylacetate and petroleum spirit yielded pure white crystals (255 mg, yield 84%). m.p. 145.4° C.-146.3° C.

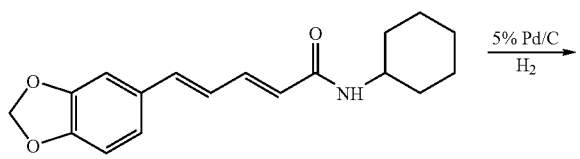

5-(3,4-methylenedioxy phenyl)-2E, 4E-pentadienoic acid cyclohexyl amide

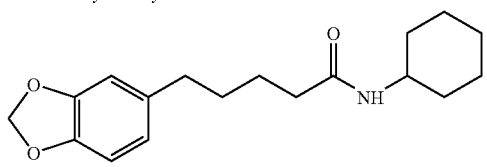

5-(3,4-methylenedioxy phenyl)-2,4-pentanoic acid cyclohexyl amide

5. Preparation of 7-(3,4-methylenedioxy phenyl)-heptanoic acid piperidineamide (RV-C05)

To 7-(3,4-methylenedioxy phenyl)-2E,4E,6E-heptatrienoic acid piperidine amide (150 mg, 0.06 mmole) was added 5% Pd/C (15 mg) and hydrogenated the contents at 30 psi for 30 min to give 7-(3,4-methylenedioxy phenyl)-heptanoic acid piperidine amide as an oil.

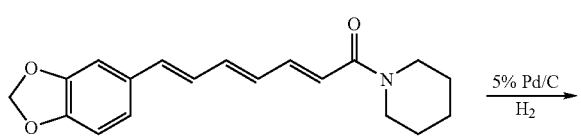

7-(3, 4-methylenedioxy phenyl)-2E, 4E, 6E-heptatrienoic acid piperidine amide

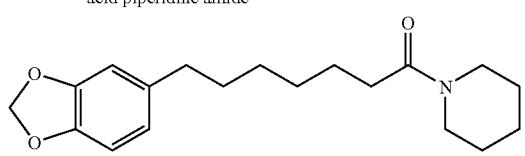

7-(3,4-methylenedioxy phenyl)-2,4,6-heptanoic acid piperidine amide

RV-C04

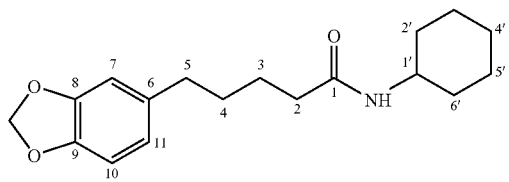

$^1$H-NMR (CDCl$_3$) δ: 6.65 (d, 1H J=1.6, Ar-7-H), 6.71 (d, 1H J=7.8, Ar-10-H), 6.60 (d, d, 1H J=1.6, 8.0 Ar-11-H), 5.90 (s, 2H, O—CH$_2$—O), 5.43 (s, 1H, NH), 2.53 (t, 2H, J=7.7 (CH$_2$—CH$_2$—CH$_2$CH$_2$)) 2.14 (t, 2H, J=7.7 ((CH$_2$—CH$_2$—CH$_2$—CH$_2$)) 1.62-1.91 (m, 10H, CH$_2$—CH$_2$—CH$_2$, CH$_2$—CH$_2$—CH$_2$ (cyclohexyl amide) 1.07-1.30 (m, 4H, CH$_2$—CH$_2$—CH$_2$ (cyclohexylamide)) $^{13}$C-NMR (CDCl$_3$): 25.3 ((CH$_2$)$_2$), 25.7 (CH$_2$), 25.9 (CH$_2$), 31.3 (CH$_2$), 31.7 (CH$_2$), 33.6 (CH$_2$), 35.8 (CH$_2$), 37.3 (CH$_2$), 48.4 (CH), 101.1 (CH$_2$), 108.4 (CH), 109.2 (CH), 121.4 (CH), 136.4 (C), 145.8 (C), 147.8 (C), 172.2 (C), MS m/z (%): 303 (M$^+$ 98), 204 (72), 176 (13), 168 (16), 162 (12) 161 (14), 154 (27), 148 (66), 141 (61) 135 (100) 74 (24) 60 (60)

RV-C05

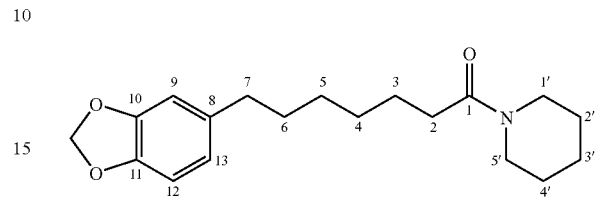

$^1$H-NMR (CDCl$_3$) δ: 6.66 (d, 1H J=1.5, Ar-7-H), 6.71 (d, 1H J=7.8, Ar-10-H), 6.60 (d, d, 1H J=1.6, 8.0 Ar-11-H), 5.90 (s, 2H, O—CH$_2$—O), 3.53 (t, 2H, J=5.4 CH$_2$—N—CH$_2$) 3.37 (t, 2H, J=5.7, (CH$_2$—N—CH$_2$) 2.51 (t, 2H, J=7.7 (CH$_2$—CH$_2$—CH$_2$—CH$_2$—CH$_2$—CH$_2$)) 2.33(t, 2H, J=7.7 ((CH$_2$—CH$_2$—CH$_2$—CH$_2$—CH$_2$—CH$_2$)) 1.52-1.65 (m, 10H, hydrocarbon CH$_2$, CH$_2$, CH$_2$—CH$_2$—CH$_2$ (Piperidine)) 1.34 (m, 4H, CH$_2$CH$_2$) $^{13}$C-NMR (CDCl$_3$): 24.9 (CH$_2$), 25.8 (CH$_2$), 25.9 (CH$_2$), 26.9 (CH$_2$), 29.3 29.7 (CH$_2$), 31.3 (CH$_2$), 31.9 (CH$_2$), 33.8 (CH$_2$), 42.9 (CH$_2$), 47.1 (CH$_2$), 101.8 (CH$_2$), 108.4 (CH), 109.2 (CH), 121.4 (CH), 137.0 (C), 145.7 (C), 147.8 (C), 171.8 (C), MS m/z (%): 317 (M$^+$ 78), 232 (11), 204 (10), 183 (30), 182 (15), 154 (21) 148 (43), 141 (41), 127 (100), 112 (43), 85 (49) Yield 51.2%

The invention claimed is:

1. A compound having the formula

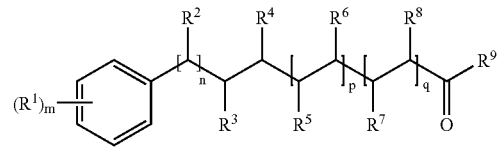

in which
m is 2;
n is 0 or 1;
p is 1;
q is 0 or 1;
the two $R^1$ groups together represent 3',4'-methylenedioxy group;
$R^2$ is hydrogen;
$R^3$ and $R^4$ represent hydrogen atoms or together represent a carbon to carbon double bond;
$R^5$ and $R^6$ represent hydrogen atoms or together represent a carbon to carbon double bond;
$R^7$ and $R^8$ represent a carbon to carbon double bond; and
$R^9$ represents cyclohexylamino wherein at least one of $R^3$ and $R^4$ together and
$R^5$ and $R^6$ together represent a carbon to carbon double bond.

2. A compound according to claim 1, wherein n is 0.

3. A compound according to claim 2, wherein q is 0 and $R^3$ and $R^4$ together and $R^5$ and $R^6$ together represent a carbon double bond.

4. A compound according to claim 1, wherein said compound is 5-E,E-piperinoylcyclohexylamine.

5. A compound according to claim 1, being 5-(3,4-methylenedioxyphenyl)-2E,4E-pentadienoic acid cyclohexylamide, or 7-(3,4-methylenedioxyphenyl)-2E,4E,6E-heptatrienoic acid cyclohexylamide.

6. A compound having the formula

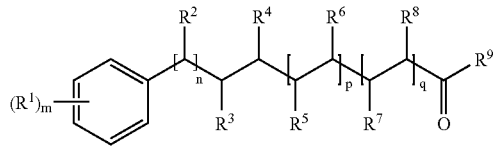

in which
m is 2;
n is 0 or 1;
p is 0 or 1;
q is 0 or 1;
the two $R^1$ groups together represent a 3',4'-methylenedioxy group;
$R^2$ to $R^8$ are hydrogen atoms; and
$R^9$ represents cyclohexylamino.

7. A compound according to claim 6, wherein said compound is 5-(3,4-methylenedioxyphenyl)-pentanoic acid cyclohexylamide or 7-(3,4-methylenedioxyphenyl)-heptanoic acid cyclohexylamide.

8. A pharmaceutical composition comprising a therapeutically effective amount of a compound of claim 1 and a pharmaceutically acceptable carrier.

9. A pharmaceutical composition according to claim 8, in which the pharmaceutically acceptable carrier includes glycerol.

10. A pharmaceutical composition according to claim 8, in which the pharmaceutically acceptable carrier includes ethanol.

11. A pharmaceutical composition according to claim 8, which includes a skin penetration enhancer.

12. A pharmaceutical composition according to claim 8 in the form of a lotion.

13. A pharmaceutical composition according to claim 12, comprising 0.03 to 3.0 mg % w/w of the compound.

14. A method of treating melanoma of the skin or vitiligo in an animal or human comprising administering a therapeutically effective amount of a compound of claim 1 to said animal or human.

* * * * *